United States Patent
Hoffeins

(10) Patent No.: US 11,679,035 B2
(45) Date of Patent: Jun. 20, 2023

(54) TOP BAND FOR GARMENTS, IN PARTICULAR FOR MEDICAL COMPRESSION STOCKINGS OR BANDAGES

(71) Applicant: MEDI GMBH & CO. KG, Bayreuth (DE)

(72) Inventor: Peter Hoffeins, Bayreuth (DE)

(73) Assignee: MEDI GMBH & CO. KG, Bayreuth (DE)

( * ) Notice: Subject to any disclaimer, the term of this patent is extended or adjusted under 35 U.S.C. 154(b) by 1033 days.

(21) Appl. No.: 16/367,248

(22) Filed: Mar. 28, 2019

(65) Prior Publication Data

US 2019/0298583 A1    Oct. 3, 2019

(30) Foreign Application Priority Data

Apr. 3, 2018 (EP) .................... 18020129

(51) Int. Cl.
*A61F 13/08* (2006.01)
*A41B 11/00* (2006.01)
(Continued)

(52) U.S. Cl.
CPC ............ *A61F 13/08* (2013.01); *A41B 11/008* (2013.01); *A41B 11/123* (2013.01);
(Continued)

(58) Field of Classification Search
CPC .......... A61F 13/00; A61F 13/02; A61F 13/06; A61F 13/08; A61F 13/00051; A61F 13/0269; A61F 13/0273; A41B 11/00; A41B 11/008; A41B 11/12; A41B 11/121; A41B 11/123; A41B 11/125; A41B 11/126; A41B 11/128; A41B 11/14; A41B 11/143; A41B 11/146; A41B 2300/32; A41B 2300/52; A41B 2500/00; D03D 1/00; D03D 1/0094; D03D 3/00; D03D 3/005;
(Continued)

(56) References Cited

U.S. PATENT DOCUMENTS 2,173,468 A * 9/1939 Bennett ..................... A41F 9/00
                                                                 2/221
3,800,331 A * 4/1974 Taddeo ................... A61F 13/08
                                                                 2/240
(Continued)

FOREIGN PATENT DOCUMENTS

DE          2505923 C2    11/1986
DE      202004014731 U1   12/2004

*Primary Examiner* — Ophelia A Hawthorne
*Assistant Examiner* — Gina Mccarthy
(74) *Attorney, Agent, or Firm* — Rimon PC

(57) ABSTRACT

A top band (1, 1') for garments (2), in particular for medical compression stockings or bandages, comprising a flexible basic body (3, 3') with an inside (4, 4') facing the garment (2) and an outside (5, 5'), wherein the flexible basic body (3, 3') comprises a fastening section (7, 7') for the garment (2) on the inside (4, 4') next to a coupling section (6, 6'), and wherein the fastening section (7, 7') is formed by an edge-side recess (8, 8') in the flexible basic body (3, 3'), so that the garment (2) can be fastened, offset from the coupling section (6, 6') of the flexible basic body (3, 3'), in the recess (8, 8').

19 Claims, 2 Drawing Sheets

Figure 1:
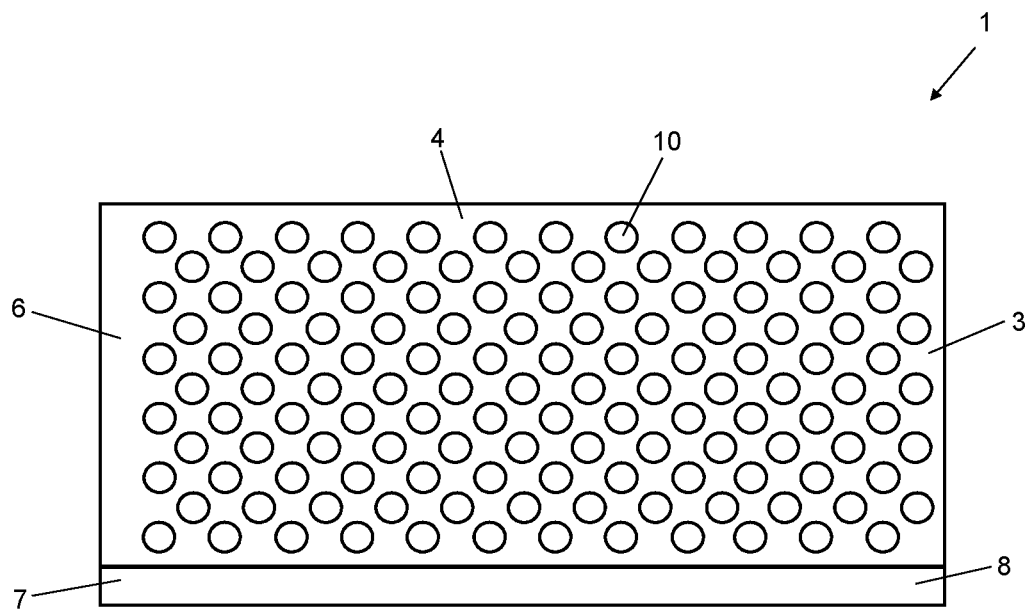

(51) Int. Cl.
   *A41B 11/12* (2006.01)
   *D03D 1/00* (2006.01)
   *D03D 3/04* (2006.01)
   *A61F 13/02* (2006.01)
   *A61F 13/00* (2006.01)

(52) U.S. Cl.
   CPC .... *A61F 13/00051* (2013.01); *A61F 13/0269* (2013.01); *A61F 13/0273* (2013.01); *D03D 1/00* (2013.01); *D03D 3/04* (2013.01); *A41B 2300/52* (2013.01); *A41B 2400/32* (2013.01); *A41B 2500/20* (2013.01); *D10B 2501/06* (2013.01)

(58) Field of Classification Search
   CPC .... D10B 2501/06; D04B 11/28; D04B 1/265; A41F 13/00; A41F 9/00
   See application file for complete search history.

(56) References Cited

U.S. PATENT DOCUMENTS

| | | | | |
|---|---|---|---|---|
| 4,514,863 | A * | 5/1985 | Tuyet-Van | A41B 11/00 2/240 |
| 6,673,421 | B1 * | 1/2004 | Andrews | D04B 1/265 442/101 |
| 2012/0058316 | A1 * | 3/2012 | Cherneski | D04B 11/28 427/288 |

* cited by examiner

TOP BAND FOR GARMENTS, IN PARTICULAR FOR MEDICAL COMPRESSION STOCKINGS OR BANDAGES

CROSS-REFERENCE TO RELATED APPLICATIONS

This application claims priority to European Patent Application serial no. 18 020 129.5 filed Apr. 3, 2018, the contents of which is incorporated herein by reference in its entirety as if set forth verbatim.

The present invention relates to a top band for garments, in particular for medical compression stockings or bandages according to the preamble of claim 1, as well as to a garment, in particular a compression stocking or bandage according to claim 11.

Garments of this kind, in particular garments such as compression stockings, in particular serve the purpose of selectively applying pressure to the body of a patient. The aim is to provide relief to a damaged venous and/or lymphatic system of a patent. Bandages are used for stabilising, relieving, calming, guiding and/or correcting limbs of a patient. These medical garments are preferably formed from so-called knitted fabrics, which are produced as flat knits or circular knits on a flat or circular knitting machine.

In order to prevent these garments, in particular compressive garments, from slipping on a patient's body, so-called top bands or adhesive lace tapes are known. These are attached to the edge of the garments, in particular by sewing them on to the compressive knitted fabrics thereof. The top bands as such are normally manufactured from a material, which is elastic in longitudinal direction and rather more inelastic in transverse direction. Due to the elasticity of the top bands in longitudinal direction, these tapes do not present a problem in view of putting on the garments. The low transverse elasticity and an adhesive effect ensure that the, in particular compressive, garment is held securely on the body of the patient.

Such a top band for an undergarment, in particular for orthopaedic purposes, is known from the DE 20 2004 014 731 U1.

The known lace tape is formed from a lengthwise elastic basic knit of constant cross-section and preferably connected to a garment via a seam, in that it extends past the garment on the edge, i.e. is arranged so as to overlap when sewn on. The side of the lace tape, which is next to the skin, has an adhesive layer, which consists of two silicone strips applied in longitudinal direction. Due to the adhesive layer in contact with the skin slipping of the garment is avoided.

The DE 25 05 923 C2 also discloses a top band for garments.

The elastic top band has an elastic basic body made of a textile woven fabric, which in addition has a non-gliding elastomer applied to it, in particular on the inside thereof. The tape as such is connected to the garment via a seam. To this end the garment can be optionally sewn onto the inside of the tape or brought into contact with the face-side of the tape and connected with the elastic tape by a seam. This tape also has an elastic basic body with a constant diameter across the entire width.

The disadvantage of this design of top bands and lace tapes lies in the connection between top band and garment. The known design of the elastic basic body of the top bands, which is characterised by a constant cross-section across the entire width of the tapes, as well as by the fastening to the inside of the basic body of the top bands leads to a bulky connection point. The garment as well as the seam material reaches beyond the inside of the top band. This leads to an undesirable bulge being formed, which when wearing the garments is perceived as annoying by the patient.

Also the face-side edge-to-edge connection of the garment with the top band, in particular its basic body, known in particular from the DE 25 05 923 C2, in order to avoid a bulky connection as far as possible, has its disadvantages. As a result of pulling on the top band, in particular when putting on compressive garments with high tensile forces, visible gaps are created between top band and garment. These gaps in the garment are undesirable. Furthermore, in comparison to the overlapping fastening of the garment on the top band, such a seam is less strong.

The object of the present invention is to propose a top band, in particular for medical compression stockings or bandages, which avoids the disadvantages of the state of the art, in particular improves the wearing comfort of the top band, the optical effect in the seam region, in particular when the garment is worn, as well as the durability and the strength of the seam.

According to one embodiment of the top band for garments, in particular for medical compression stockings or bandages, this comprises a flexible basic body with an inside which faces the garment as well as an outside, wherein the flexible basic body on the inside, comprises both a coupling section and a fastening section for the garment and wherein the fastening section is formed in the flexible basic body by an edge-side recess, so that the garment can be fastened, in particular as regards height, offset from the coupling section of the flexible basic body in the recess.

According to a first embodiment the flexible basic body is formed from a textile woven fabric consisting of a number of warp threads and at least one weft thread inserted between the threads. Alternatively, it is also possible for the top band to be formed from a knitted basic body, optionally in the "Raschel" technique. If it is a woven fabric, the weft thread of the textile woven fabric preferably extends essentially across the entire width of the top band. In other words, the weft thread is arranged in the flexible basic body both in the coupling section and in the fastening section. This has the advantage that the fastening section is firmly connected to the coupling section thereby significantly improving the durability of the seam, which, in particular when putting on compressive garments with high tensile forces, is of particularly great importance.

Preferably, the flexible basic body of the top band is elastic in longitudinal direction and essentially inelastic in transverse direction, so that the top band is not a hindrance when putting on the garment attached to it, and at the same time ensures that the in particular compressive garment is reliably held in place on a patient's body.

According to a second embodiment of the top band an anti-slip coating is applied, at least in sections, to the coupling section of the flexible basic body. This preferably takes the form of patterned, in particular knob-type or line-type adhesive coupling regions. The coating preferably comprises a height of approx. 0.5 mm. In particular, the offset arrangement of the fastening section relative to the coupling section, in particular in a garment to be fastened to the top band in the edge-side recess in the flexible basic body, allows the anti-slip coating to be given a particularly flat shape, since it is easy for the coating to protrude relative to the inside of a garment attached to the top band. This brings with it the added advantage that due to strongly protruding patterns, such as in particular knobs, pressure points on the skin are very largely avoided as a result of the flat anti-slip coating.

Fastening of a garment, in particular a knitted fabric in the recess of the flexible basic body of the top band, is made possible in that the recess has a width of at least approx. 5 mm. The height of the recess is preferably approx. 0.5-1.5 mm.

According to a further embodiment of the top band the flexible basic body is formed in one piece. The coupling section and the fastening section are formed as a single basic body. Alternatively, it is also possible that the fastening section, in particular in the form of a lip, is attached to the coupling section of the basic body.

Here it would be possible for the lip to be sewn or welded onto the coupling section. According to a preferred variant of the one-piece design of the flexible basic body the flexible body preferably further comprises a continuous surface on its outside which stretches across the entire width. In other words the outside is preferably devoid of any offset, step or recess between the coupling section and the fastening section. In addition various materials can of course be applied to the outside of the flexible basic body or inserted or worked into the surface of the basic body, in order to produce patterned surfaces.

According to one embodiment of a garment, in particular a medical compression stocking or bandage, this comprises a top band with an edge-side recess according to one of the preceding embodiments.

To this end the garment is preferably fastened to the top band by means of a form-lock connection, in particular by means of a seam. Alternatively a material-lock connection may be possible, in particular in the form of welding, gluing and/or vulcanisation. The minimum requirement for the proposed or further alternative fastening methods consists in that there must be sufficient resistance to withstand the tensile forces which are created by pulling on the top band when the garment is put on.

Furthermore it is preferred if a connection with the garment is made only in the edge-side fastening section of the top band. The connection in this case therefore does not extend into the coupling section, but is formed merely in the set-back fastening section relative to height. The width of the seam can however vary and can extend past the fastening section into the garment.

According to a further embodiment of the garment the connection between garment and top band is designed such that the inside of the garment is arranged essentially flush with the coupling section of the flexible basic body. Because the recess in the top band is designed to correspond to the thickness of the garment, in particular the thickness of the fabric, an overhang of the garment beyond the inside of the coupling section of the top band is avoided. Pressure points resulting from fastening the garment to the top band cannot therefore occur when wearing the garment.

According to a further embodiment of the garment the connection between garment and top band is designed such that the anti-slip coating applied to the flexible basic body of the top band reaches past the inside of the garment. Preferably the coating comprises a height of approx. 0.5 mm. As previously mentioned the offset arrangement of the garment in the edge-side recess in the flexible basic body allows the anti-slip coating to be formed particularly flat because it is easily possible that the coating extends beyond the inside of the garment.

The present top band for garments, in particular for medical compression stockings or bandages, is characterised by a number of considerable advantages.

Due to designing the top band in the form of a flexible basic body with a coupling section and a fastening section, wherein the fastening section is formed by an edge-side recess in the flexible basic body, so that a garment can be fastened on the top band offset to the coupling section in the recess, the wear comfort of the top band, in particular of the garment connected thereto, is substantially increased. The undesirable formation of a bulge as known from the state of the art and which is perceived as annoying by a patient who wears the garment, is avoided by the top band according to the invention.

A further advantage of the invention, in comparison to the face-side edge-to-edge connection of the garment with the top band, where an overlapping fastening is as far as possible avoided in order to avoid pressure points, consists in the distinctly improved durability and strength of the seam, which is of major importance in particular when high tensile forces develop as the garment is put on. The top band according to the invention combines the advantages of an overlapping connection with a face-side/edge-to-edge connection.

A further advantage, which results from the top band according to the invention, consists in that a distinctly improved optical effect is ensured in the fastening region in particular in the seam region when using a seam as the connection. With the face-side/edge-to-edge connection known from the state of the art, the high tensile forces developing when the garment connected to the top band is put on, result in a stretching of the seam, which leads to a visible gap between top band and garment. With the top band according to the invention, in particular the possibility of fastening the garment to/in the top band integrally, such a gap is prevented from developing, in particular when the garment is put on.

Figure 2:
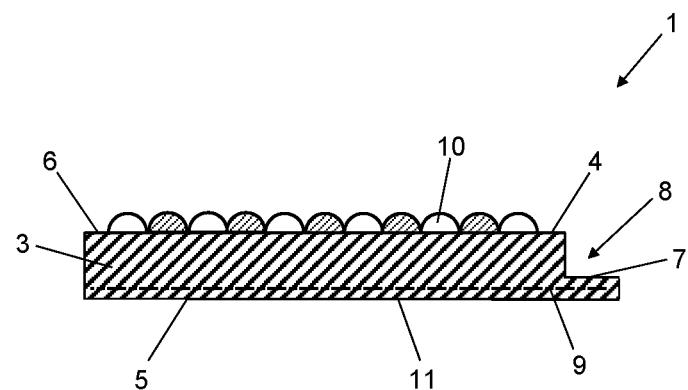
Figure 3:
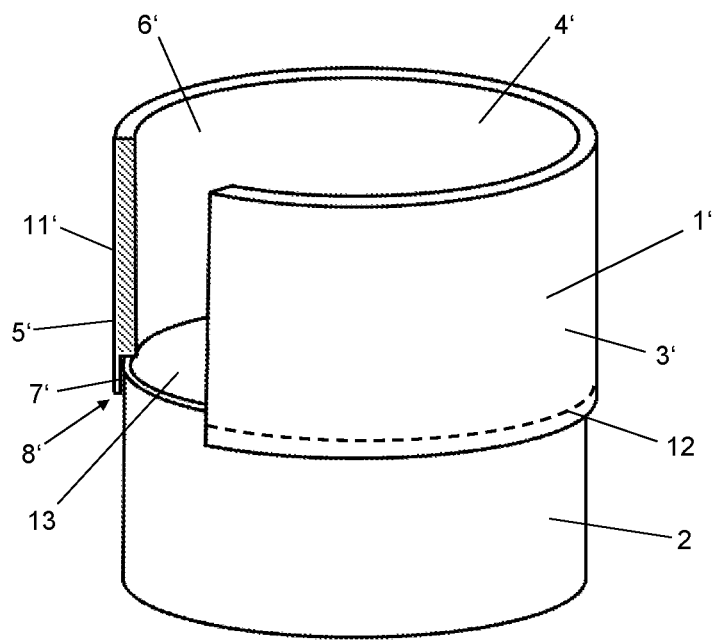
Figure 4:
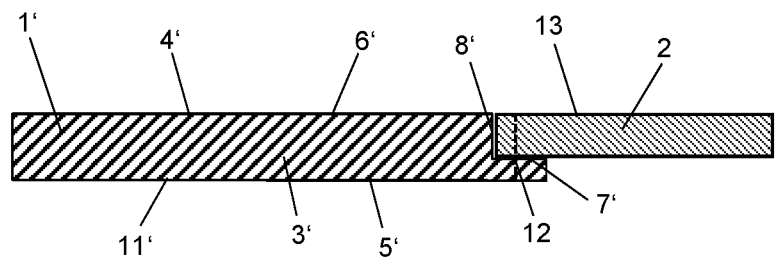

The invention will now be explained by way of a number of exemplary embodiments and in conjunction with the attached drawings, in which FIG. 1 shows a first embodiment of the top band for garments, in particular for medical compression stockings or bandages, in a top view, FIG. 2 shows a sectional view through the embodiment of the top band for garments shown in FIG. 1, FIG. 3 shows a three-dimensional depiction of the second embodiment of the top band, attached to a garment, wherein the top band is cut open in sections, FIG. 4 shows a sectional view of the second embodiment of the top band for garments, as shown in FIG. 3.

The top band 1 schematically shown in FIG. 1, in particular for medical compression stockings or bandages, comprises a flexible basic body 3 with an inside 4 facing a garment. The inside 4 consists of a coupling section 6 and a fastening section 7. The fastening section 7 is formed by an edge-side recess 8 in the flexible basic body 3. The recess 8 preferably comprises a width of at least approx. 5 mm. The height of the recess 8 is preferably at least approx. 0.5 mm. Edge-side is understood to mean a portion, which is situated at the upper or lower edge of the top band 1 and which extends as far as the upper or lower end of the top band 1. The fastening section 7 is thus not surrounded on both sides by a coupling section 6 and is thus not arranged in the interior of the top band. Due to the edge-side recess 8 a garment, in particular a knitted fabric, can be fastened to the top band 1, offset as regards height from the coupling section 6 of the flexible basic body 3 in the recess 8. The coupling section 6 preferably comprises an anti-slip coating 10, which is applied to the coupling section 6. In this embodiment the coating is designed in the form of knob-shaped adhesive coupling regions.

FIG. 2 shows the top band 1 for a garment as in FIG. 1 in a sectional view. The cross-section shows that the coupling section 6 and the fastening section 7 are arranged in/on the flexible basic body 3, offset from one another as regards height by an edge-side recess/setback 8. The recess 8, which is formed on the side 4 of the top band 1 facing the skin of the patient, forms a lip-shaped fastening section 7 on the top band 1, in particular the flexible basic body 3. The fastening section/the lip 7 with a cross-section reduced relative to the remaining cross-section of the top band 1 is preferably formed in one piece with the flexible basic body 3. Alternatively, it is possible for the part of the flexible basic body 3 comprising the reduced cross-section to be glued, sewn, or woven onto the top band 1.

The flexible basic body 3 is preferably formed in one piece from a textile woven fabric consisting of a number of warp threads and at least one weft thread 9 inserted between the threads. The at least one inserted weft thread 9 essentially extends across the entire width of the top band 1. Therefore this is arranged both on the coupling section 6 and on the fastening section 7, whereby the hold of the fastening section 7 on the coupling section 6, i.e. the lip on the top band 1, is distinctly increased. The basic body 3 as such is preferably elastic in longitudinal direction and essentially inelastic in transverse direction.

The sectional view also shows the anti-slip coating 10 on the inside 4 of the top band 1, in particular it shows a cut through the knob-shaped adhesive regions. On the opposite outside 5 of the top band 1 this shows an, in particular single, continuous surface 11. This surface 11, which preferably is essentially designed without projections or setbacks, forms a common outside 5 for the coupling section 6 and the fastening section 7. This has the advantage that a garment, in particular a knitted fabric, can be fastened very discretely and without showing up, on the top band 1.

FIG. 3 shows a three-dimensional view of a second exemplary embodiment of the top band 1', attached to a garment 2, wherein the top band 1' is cut open in sections. Preferably the garment 2 is a medical circular-knitted or flat-knitted arm or leg stocking, in particular a compression stocking consisting of a compressive knitted part in order to provide relief for a patient's damaged venous and/or lymphatic system. Compression stockings of this kind for a leg consist of a foot part and a calf part. Alternatively it is also possible for the foot part and the calf part to be detachably connected to each other. The compression stocking is preferably associated with one of the standardised four compression classes. The garment 2, in particular the hold-up compression stocking, is preferably positively connected to the top band 1' by means of a seam, in order to ensure that the stocking is securely held on a leg or arm of a patient.

In this embodiment also the top band 1' comprises a flexible basic body 3' with an inside 4' and an outside 5'. The outside 5' may have various pattern worked into, or applied to the basic body 3' for decorative purposes. On the inside 4' the top band comprises a coupling section 6' and a fastening section 7'. The coupling section 6' here is preferably designed without an additional anti-slip coating. In this embodiment the material of the flexible basic body 3' itself comprises anti-slip properties. The fastening section 7' is formed by the edge-side recess 8', which extends around the entire top band 1', in particular around the entire top band section 1', which is needed in order to form a circular coupling region on the sleeve-like garment 2. The elongated top band 1' is preferably closed by means of a transverse seam in order to form a sleeve-like region on the garment 2. The recess 8' is configured such that the garment 2 can be sewn onto it and can be received as a whole in the recess 8', so that it does essentially not extend beyond the inside 4' of the top band 1'. The inside 13 of the garment 2 is thus essentially connected flush with the inside 4' to the top band 1'. On the outside 5' the top band 1' again comprises a continuous surface 11' in this embodiment also.

FIG. 4 shows a sectional view of the second embodiment of the top band 1', which is connected to a garment 2.

As already described, the garment 2 is connected to the top band 1' by means of a seam 12 such that the inside 13 of the garment 2 is essentially flush with the inside 4' of the according to a further embodiment of the flexible basic body 3' of the top band 1', i.e. is attached to the top band 1' only by a minimum overhang or rearward offset. The fastening section 7' in this embodiment is again implemented by an edge-side recess 8' in the form of a setback or step in the flexible basic body 3'. The step-shaped implementation of the basic body 3' permits a height-related offset between coupling section 6' and fastening section 7'. Further shapes of the recess 8' are of course possible. The preferred shape of the recess however, is a step. The coupling section 6' in this embodiment is implemented by an anti-slip basic body 3', which means that the material of the flexible basic body 3' itself already comprises anti-slip properties. An additional anti-slip coating is therefore not necessary. If the basic body 3' is produced from a woven fabric, the plurality of wrap threads of the fabric already has anti-slip surfaces. Here again it can be clearly seen that the top band 1' comprises a continuous surface 11' on the outside 5' in the region of the coupling section 6' and the fastening section 7', so that the garment 2 can be fastened to the top band 1' in such a manner that it does not show up.

The invention is not limited to the embodiments described, but comprises all designs, in which functional the principle of the invention is analogously applied or included. Furthermore all features of all described and depicted exemplary embodiments can be combined with one another.

The invention claimed is:

1. A top band for a garment comprising a flexible basic body with an inside facing the garment and an outside, the garment defined by an outside surface, a top section having a top, and an inside surface, wherein the flexible basic body comprises a fastening section for the top section of the garment on the inside next to a coupling section, characterised in that the fastening section is formed by an edge-side recess on the inside of the flexible basic body, wherein the edge-side recess is formed such that a thickness of the flexible basic body at the recess is smaller than a thickness of the flexible basic body at other locations, so that the top section of the garment can be fastened to the top band at the edge-side recess and, upon being fastened to the top band, is surrounded by the top band on the outside surface of the top section and the top, wherein the garment and the coupling section form a uniform surface on the inside when the garment is attached to the fastening section, and wherein the top section of the garment is not surrounded on the inside surface by the top band.

2. The top band for garments according to claim 1, characterised in that an anti-slip coating is applied, at least in sections, to the coupling section of the flexible basic body.

3. A garment, comprising a top band according to claim 2.

4. The garment according to claim 3, characterised in that the garment is fastened to the top band by means of a material-lock connection, or by means of a form-lock connection.

5. The garment of claim 4, wherein the material-lock connection is by welding, gluing, or vulcanizing.

6. The garment of claim 4, wherein the form-lock connection is by means of a seam.

7. The garment according to claim 3, characterised in that a connection between the top band and the garment is made only in the fastening section of the top band.

8. The garment according to claim 3, characterised in that the connection between the garment and the top band is designed such that the inside of the garment is arranged essentially flush with the coupling section of the flexible basic body of the top band.

9. The garment according to claim 3, characterised in that a connection between the garment and the top band is designed such that the anti-slip coating applied to the flexible basic body of the top band extends beyond the inside of the garment.

10. The top band for garments according to claim 2, characterised in that the anti-slip coating is formed by knob-shaped or line-shaped coupling regions.

11. The top band for garments according to claim 1, characterised in that the flexible basic body is formed from a textile woven fabric consisting of a number of warp threads and at least one weft thread inserted between the threads.

12. The top band for garments according to claim 11, characterised in that the weft thread of the textile woven fabric substantially extends across an entire width of the top band.

13. The top band for garments according to claim 1, characterised in that the flexible basic body is elastic in longitudinal direction and substantially inelastic in transverse direction.

14. The top band for garments according to claim 1, characterised in that the recess has a width of at least approximately 5 mm.

15. The top band for garments according to claim 1, characterised in that the recess has a height of at least approximately 0.5 mm.

16. The top band for garments according to claim 1, characterised in that the flexible basic body is formed in one piece.

17. The top band for garments according to claim 1, characterised in that the flexible basic body, on the outside of the flexible basic body, comprises a continuous surface across the flexible basic body's entire width.

18. The garment of claim 1, wherein the flexible basic body is elastic in a longitudinal direction and essentially inelastic in a transverse direction.

19. The garment of claim 1, wherein the flexible basic body is formed in one piece as a single basic body.

* * * * *